United States Patent [19]

Hirota et al.

[11] Patent Number: 4,782,179

[45] Date of Patent: Nov. 1, 1988

[54] 3-AMINO-2,4,5-TRIFLUOROBENZOIC ACID AND A METHOD FOR MANUFACTURE THEREOF

[75] Inventors: Koichi Hirota, Suita; Osamu Kaieda, Osaka; Tsuguo Takaya, Ohtsu, all of Japan

[73] Assignee: Nippon Shokubai Kagaku Kogyo Co., Ltd., Japan

[21] Appl. No.: 153,975

[22] Filed: Feb. 9, 1988

[30] Foreign Application Priority Data

Feb. 13, 1987 [JP] Japan .................................. 62-29582

[51] Int. Cl.$^4$ .......................................... C07C 101/54
[52] U.S. Cl. .................................................. 562/456
[58] Field of Search ........................................ 562/456

[56] References Cited

U.S. PATENT DOCUMENTS

| 3,459,794 | 8/1969 | Tamborski | 562/456 |
| 4,359,428 | 11/1982 | Jacobs et al. | 562/456 |
| 4,521,616 | 1/1985 | Fifolt et al. | 562/456 |

FOREIGN PATENT DOCUMENTS 0053247  6/1982  European Pat. Off. ............ 562/456

*Primary Examiner*—James H. Reamer
*Attorney, Agent, or Firm*—Omri M. Behr

[57] ABSTRACT

3-amino-2,4,5-trifluorobenzoic acid which is a novel compound and is manufactured by heating 4-amino-3,5,6-trifluorophthalonitrile in the presence of an acid.

13 Claims, 1 Drawing Sheet

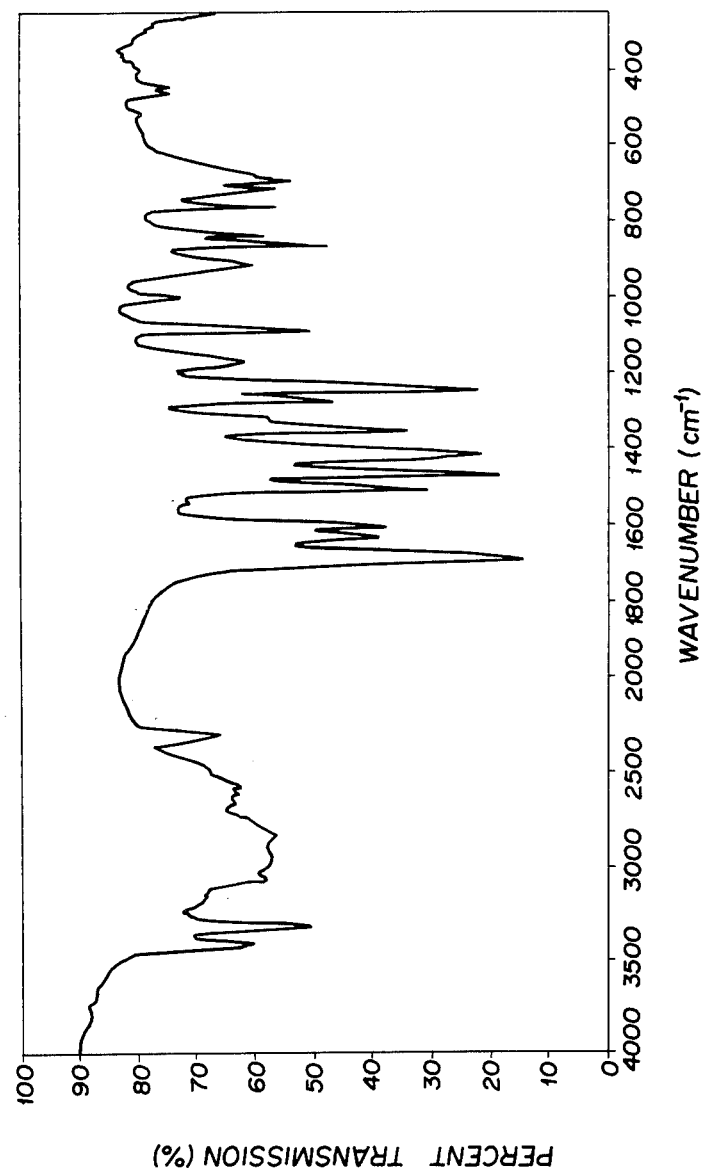

3-AMINO-2,4,5-TRIFLUOROBENZOIC ACID AND A METHOD FOR MANUFACTURE THEREOF

BACKGROUND OF THE INVENTION

1. Field of the Invention

The present invention relates to novel 3-amino-2,4,5-trifluorobenzoic acid and a method for manufacture thereof.

2. Description of the Prior Art 3-amino-2,4,5-trifluorobenzoic acid in accordance with the present invention is a novel compound, so the compound itself and a method for manufacture thereof have not yet been reported.

An object of the present invention is, accordingly, to provide novel 3-amino-2,4,5-trifluorobenzoic acid and a method for manufacture thereof.

SUMMARY OF THE INVENTION

The above-mentioned object can be attained by 3-amino-2,4,5-trifluorobenzoic acid.

The object can also be attained by a method for manufacturing 3-amino-2,4,5-trifluorobenzoic acid by subjecting 4-amino-3,5,6-trifluorophthalonitrile to heat in the presence of an acid.

The novel 3-amino-2,4,5-trifluorobenzoic acid provided by the present invention is useful as a starting material or intermediate for synthesizing a pharmaceutical, especially an antimicrobial agent. 3-Amino-2,4,5-trifluorobenzoic acid is also useful as a monomer for preparation of a polyamide, because it has both amino and carboxyl groups in the molecule.

BRIEF DESCRIPTION OF THE INVENTION

Single FIGURE is an infrared absorption spectrum chart of 3-amino-2,4,5-trifluorobenzoic acid.

EXPLANATION OF THE PREFERRED EMBODIMENT 3-amino-2,4,5-trifluorobenzoic acid of this invention can be manufactured by heating 4-amino-3,5,6-trifluorophthalonitrile in the presence of an acid. As the acid, any acid which is usually used in general hydrolysis such as an inorganic acid, e.g., sulfuric acid, hydrogen chloride and phosphoric acid can be used, and sulfuric acid is preferable. The acid is usually used as aqueous solution.

Typically, novel 3-amino-2,4,5-trifluorobenzoic acid can be manufactured by heating 4-amino-3,5,6-trifluorophthalonitrile in an aqueous sulfuric acid solution at a temperature of 90° to 170° C. based on hydrolysis and further of decarboxylation.

It is assumed that the reaction proceeds by hydrolysis and decarboxylation at the same time as shown in an equation I to form 3-amino-2,4,5-trifluorobenzoic acid.

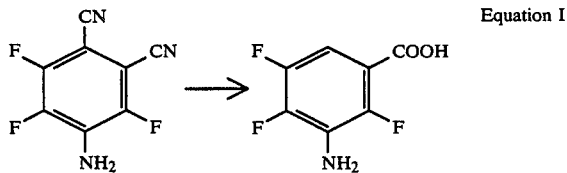

Equation I

Concentration of the aqueous acid solution is 20 to 90% by weight, preferably 40 to 70% by weight. If the concentration of the acid exceeds 90% by weight, sudden reaction is apt to occur and generates heat, so it is dangerous. If the concentration is less than 20% by weight, reaction rate decreases and productivity remarkably decreases, so it is not preferable. Therefore, it is preferable to select an appropriate concentration of the acid.

The reaction temperature is 90° to 170° C., preferably 110° to 150° C. If the temperature is exceeds 170° C., sudden reaction occurs and generates heat, so it is dangerous. If the temperature is less than 90° C., reaction rate and productivity decrease, so it is not preferable.

It is usually preferable that the reaction is carried out under reflux and under normal pressure. When the reaction is carried out under reflux, the reaction temperature is especially depended on the acid concentration, but the reaction may be carried out under high or reduced pressure in order to avoid the dependance of the acid concentration. Further, when the reaction is carried out under normal pressure, it is not always carried out under reflux, and it may be carried out by controlling less temperature.

Reaction time is not limited, it is preferable 3 to 30 hours, more preferable 10 to 20 hours.

Feeding concentration of 4-amino-3,5,6-trifluorophthalonitrile is preferable so as to be 100 to 1,000 parts by weight, preferably 200 to 700 parts by weight of the aqueous acid solution per 100 parts by weight of 4-amino-3,5,6-trifluorophthalonitrile. The reaction may be initiated after feeding 4-amino-3,5,6-trifluorophthalonitrile and the aqueous acid solution at the same time into a reaction zone. Further, the reaction may safely be carried out by controlling the reaction as follows:

(a) A method for reaction by adding 4-amino-3,5,6-trifluorophthalonitrile continuously or intermittently to the aqueous acid solution in a reaction zone.

(b) A method for reaction by adding the acid or the aqueous acid solution continuously or intermittently to an aqueous slurry solution of 4-amino-3,5,6-trifluorophthalonitrile in a reaction zone.

(c) A method for controlling the reaction rate by feeding both 4-amino-3,5,6-trifluorophthalonitrile and a low concentration of an aqueous acid solution to a reaction zone to initiate the reaction, and then adding the acid continuously or intermittently to the mixture with the proceeding of the reaction to vary the acid concentration and increase the reaction temperature step by step. In such case, acid concentration to be fed prior to the initiation of the reaction is preferably 10 to 70% by weight, and acid concentration to be added is preferably 40 to 98% by weight. The reaction is preferably carried out by initiating the reaction at a temperature of 90° to 140° C. and then elevating the reaction temperature to 120° to 170° C. by adding the acid gradually along with the proceeding of the reaction.

In any methods, in the reaction system, an inert organic solvent, e.g., ketones such as acetone and methyl ethyl ketone, nitriles such as acetonitrile and benzonitorile, an aprotic polar solvent such as dimethyl formamide and sulfolane, etc.

Further, although the novel compound 3-amino-2,4,5-trifluorobenzoic acid is preferably manufactured by conducting hydrolysis and decarbonylation of the starting 4-amino-3,5,6-trifluorophthalonitrile at the same time because of simple process, 4-amino-3,5,6-trifluorophthalonitrile may be previously hydrolized to produce 4-amino-3,5,6-trifluorophthalic acid and then decarboxylated it to produce 3-amino-2,4,5-trifluorobenzoic acid. Further, 4-amino-3,5,6-trifluorophthalic acid may be previously esterified to produce ester such as methyl 4-amino-3,5,6-trifluorophthalate and then decarboxylated it to produce 3-amino-2,4,5-trifluorobenzoic acid.

4-amino-3,5,6-trifluorophthalonitrile as to the starting material in the present invention is known compound and can easily be obtained by a method disclosed in Ishikawa et al, Yuki Gosei Kagaku Kyokaishi, 29, (8), 794 (1971) or Birchall et al, Journal of the Chemical Society (C), 1970, 456 (1970).

A method for manufacturing a novel compound of the present invention will be explained by the following examples in detail, and results of analysis for identifying the novel compound is also described.

It is of course that the method for manufacturing 3-amino-2,4,5-trifluorobenzoic acid is not limited the following examples.

EXAMPLE 1

Into 200 ml of a four-necked separable flask having a stirrer, a thermometer and a Dimroth condenser, 200 g of 60% by weight of aqueous sulfuric acid solution was fed and further 30.0 g (0.152 mole) of 4-amino-3,5,6-trifluorophthalonitrile was charged, then heated to elevate the temperature. The reaction was carried out under sufficiently stirring at a temperature of 128° to 130° C. under reflux for 3 hours.

After cooling the reaction mixture, it was poured into ice water, and then 3-amino-2,4,5-trifluorobenzoic acid was extracted from an aqueous solution containing 3-amino-2,4,5-trifluorobenzoic acid by using 400 ml of isopropyl ether. Isopropyl ether layer thus obtained was dried by anhydrous magnesium sulfate and then 27.7 g (0.145 mole, 95.2 mol% of yield to 4-amino-3,5,6-trifluorophthalonitrile) of 3-amino-2,4,5-trifluorobenzoic acid was obtained.

Further, it was purified by recrystallyzation with benzene-ethanol mixture solvent, and the purified 3-amino-2,4,5-trifluorobenzoic acid was analyzed to obtain physical properties and decided the structure.

Melting point: 140°–141° C.

| Elemental analysis: | C (%) | H (%) | N (%) | F (%) |
|---|---|---|---|---|
| Theoretical | 43.99 | 2.11 | 7.33 | 29.82 |
| Found | 44.12 | 2.13 | 7.41 | 29.96 |

| Infrared spectrum (KBr tablet, unit: cm$^{-1}$) | |
|---|---|
| 3420, 3335 | (amino $\nu$ —N—H) |
| 2500–3200 | (hydroxy $\nu$ —O—H) |
| 1695 | (carbonyl $\nu$ > C=O) |

Infrared absorption spectrum is shown in attached FIGURE.

$^{19}$F NMR (solvent:aceton-d$^6$, inner standard substance: CF$_3$COOH) ppm

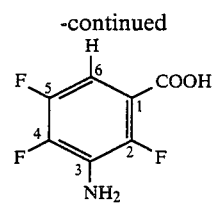

| | | |
|---|---|---|
| F$_2$ | $\delta$ | −55.87, ddd (J=19.5, 13.4, 6.4) |
| F$_4$ | $\delta$ | −73.91, ddd (J=19.5, 20.4, 8.8) |
| F$_5$ | $\delta$ | −67.90, ddd (J=13.4, 20.4, 10.7) |

EXAMPLE 2

A similar method to Example 1 was carried out except that concentration of sulfuric acid was 45% by weight, the reaction temperature was 120° C. and the reaction time was 12 hours.

As the result, 28.1 g (96.6 mol% of yield to 4-amino-3,5,6-trifluorophthalonitrile) of 3-amino-2,4,5-trifluorobenzoic acid was obtained.

EXAMPLE 3

Into 200 ml of a four-necked separable-flask having a stirrer, a thermometer and a Dimroth condenser, 200 g of 60% by weight of aqueous sulfuric acid solution was fed, heated under stirring and maintained at a temperature of 130° C. 30.0 g (0.152 mol) of 4-amino-3,5,6-trifluorophthalonitrile was added to the solution gradually for 3 hours, and then subjected to reaction for 2 hours.

Then extraction operation similar to Example 1 was carried out to obtain 27.2 g (0.142 mole, 93.5 mol% of yield to 4-amino-3,5,6-trifluorophthalonitrile) of 3-amino-2,4,5-trifluorobenzoic acid was obtained.

EXAMPLE 4

Into 200 ml of a four-necked separable flask having a stirrer, a thermometer and a Dimroth condenser, 76.3 g of water and 30.0 g (0.152 mole) of 4-amino-3,5,6-trifluorophthalonitrile were fed, and the mixture thus obtained was heated under stirring and maintained at a temperature of 100° C. Into the mixture, 123.7 g of 97% by weight of concentrated sulfuric acid was dropped for 2 hours to elevate the temperature from 100° C. to 128° C., and further the reaction was continued for 3 hours at a temperature of 128° to 130° C.

Then extraction operation similar to Example 1 was carried out to obtain 27.5 g (0.144 mole, 94.5 mol% of yield to 4-amino-3,5,6-trifluorophthalonitrile) of 3-amino-2,4,5-trifluorobenzoic acid was obtained.

EXAMPLE 5

Into 200 ml of a four-necked separable-flask having a stirrer, a thermometer and a Dimroth condenser, 140 g of 55% aqueous sulfuric acid solution was fed, and 50 g (0.254 mole) of 4-amino-3,5,6-trifluorophthalonitrile was fed, then the temperature of the mixture thus obtained was elevated and subjected to reaction under sufficiently stirring and refluxing at a temperature of 128° to 129° C. for 7 hours. Then 9.2 g of 97% by weight of concentrated sulfuric acid was added gradually during the reaction and subjected to reaction under refluxing at a temperature 131° to 134° C. for 4 hours, and further 8 g of 97% by weight of concentrated sulfuric acid was added gradually under refluxing at a temperature of 134° C. to 135° C. for 4 hours.

Then extraction operation similar to Example 1 was carried out to obtain 46.8 g (0.246 mole, 96.5 mol% of yield to 4-amino-3,5,6-trifluorophthalonitrile) was obtained.

What is claimed is:

1. 3-amino-2,4,5-trifluorobenzoic acid.
2. A method for manufacturing 3-amino-2,4,5-trifluorobenzoic acid which comprises subjecting 4-amino-3,5,6-trifluorophthalonitrile to heat in the presence of an acid.
3. A method according to claim 2, wherein said acid is used as an aqueous solution.
4. A method according to claim 3, wherein the heating is carried out at a temperature of 90° to 170° C.
5. A method according to claim 3, wherein said acid is an inorganic acid.
6. A method according to claim 5, wherein said inorganic acid is selected from the group consisting of sulfuric acid, hydrogen chloride and phosphoric acid.
7. A method according to claim 6, wherein said inorganic acid is sulfuric acid.
8. A method according to claim 3, wherein said acid is used in a concentration of 20 to 90% by weight.
9. A method according to claim 3, wherein said aqueous acid solution is used in an amount of 100 to 1,000 parts by weight per 100 parts by weight of 4-amino-3,5,6-trifluorophthalonitrile.
10. A method according to claim 2, wherein 4-amino-3,5,6-trifluorophthalonitrile and said aqueous acid solution are fed to a reaction zone at the same time.
11. A method according to claim 2, wherein 4-amino-3,5,6-trifluorophthalonitrile is fed continuously or intermittently to said aqueous acid solution in a reaction zone to conduct the reaction.
12. A method according to claim 2, wherein said acid or the aqueous acid solution is fed continuously or intermittently to the aqueous slurry solution of 4-amino-3,5,6-trifluorophthalonitrile in a reaction zone to conduct the reaction.
13. A method according to claim 2, wherein 4-amino-3,4,6-trifluorophthalonitrile and a low concentration of an aqueous acid solution are fed to a reaction zone at the same time to initiate the reaction, and then said acid or said aqueous acid solution is fed continuously or intermittently to conduct the reaction.

* * * * *